(12) United States Patent
Kim et al.

(10) Patent No.: US 9,809,811 B2
(45) Date of Patent: Nov. 7, 2017

(54) METHOD OF RANDOM CIRCULAR PERMUTATION BY MUCP-ISC AND MUCP-ISSC TRANSPOSONS

(71) Applicant: New York University, New York, NY (US)

(72) Inventors: Jin Ryoun Kim, Jericho, NY (US); Brennal Pierre, Brooklyn, NY (US); Vandan Shah, Jersey City, NJ (US)

(73) Assignee: New York University, New York, NY (US)

( * ) Notice: Subject to any disclaimer, the term of this patent is extended or adjusted under 35 U.S.C. 154(b) by 368 days.

(21) Appl. No.: 14/686,002

(22) Filed: Apr. 14, 2015

(65) Prior Publication Data
US 2016/0083763 A1 Mar. 24, 2016

Related U.S. Application Data

(60) Provisional application No. 61/979,894, filed on Apr. 15, 2014.

(51) Int. Cl.
*C12N 15/10* (2006.01)

(52) U.S. Cl.
CPC .................................. *C12N 15/102* (2013.01)

(58) Field of Classification Search
None
See application file for complete search history.

*Primary Examiner* — Christopher M Gross
(74) *Attorney, Agent, or Firm* — Laurence P. Colton; Smith Tempel Blaha LLC

(57) ABSTRACT

A method for designing circular permuted proteins using two engineered Mu transposons for easy construction of random circular permuted proteins, the two designed transposons being MuCP-ISC (Mu Circular permutation transposon with Integrated Start Codon) and MuCP-ISSC (Mu Circular permutation transposon with Integrated Start and Stop Codon).

27 Claims, 10 Drawing Sheets

A

B

METHOD OF RANDOM CIRCULAR PERMUTATION BY MUCP-ISC AND MUCP-ISSC TRANSPOSONS

STATEMENT OF RELATED APPLICATIONS

This patent application claims the benefit of U.S. Provisional Patent Application No. 61/979,894 having a filing date of 15 Apr. 2014.

The instant application contains a Sequence Listing that has been submitted electronically in ASCII format and is hereby incorporated by reference in its entirety. Said ASCII copy, created on 11 Aug. 2015, is named 48467.059U1_SL.txt, and is 11,762 bytes in size.

BACKGROUND OF THE INVENTION

Technical Field

The present invention is generally related to the field of designing circular permuted proteins and is more specifically related to the field of designing circular permuted proteins using two engineered Mu transposons for easy construction of random circular permuted proteins.

Prior Art

Circular permutation is an important method used in protein engineering that produces protein variants whose backbone is linked, via the N and C termini, and cleaved elsewhere to introduce new termini (1, 2). For example, circular permutation of thermosome and β-lactamase (BLA) created protein variants with higher expression levels, due to increased resistance to proteolysis (3, 4). Circular permutation can also be used to alter substrate specificity, as was the case with lipase B from *Candida antarctica* (CALB) (5). A circular permuted guest protein inserted into a host protein increased allosteric interactions between these two domains by altering their relative orientations (6, 7). These studies delineated the importance of circular permutation as an alternative to other protein engineering tools, such as random mutagenesis (8, 9), DNA shuffling (10), and site-directed mutagenesis (11) for creating variants with desired functions. When constructing circular permuted proteins, a peptide linker is usually incorporated at the genetic level (12). Fortunately, about 50% of single domain proteins have their N- and C-termini proximal (13), suggesting that circular permutation can be applied to a broad range of proteins. And it is possible that a backbone linkage between the two termini further apart from each other can still be made with a relatively long linker, increasing the applicability of circular permutation. While one can produce circular permutants chemically (2), recombinant circular permutation is usually more straightforward.

Not all circular permutations lead to correctly folded variants (14). In fact, the success of circular permutation heavily relies on the locations of new termini. Usually, loops distant from active sites, or other functionally sensitive regions of the protein, are preferred (7, 15). Backbone flexibility of parental proteins, which is well represented by B-factors, can also serve as an important guideline when selecting new termini for the circular permutant (3). Rational selection requires significant structural knowledge, which is not always available, and there is no well-established strategy to ensure the success of a rationally designed circular permuted protein. Instead, thorough examination of locations of potential new termini along the polypeptide backbone, followed by construction and subsequent evaluation of the random circular permuted variant, is often necessary.

A more powerful approach to designing circular permuted proteins is to use combinatorial methods to generate libraries that survey a much larger number of potential candidates. Combinatorial construction of a random circular permuted library typically involves a few characteristic steps: The 5' and 3' ends of a target gene is genetically attached with oligonucleotide sequences containing the same restriction enzyme site. Subsequently, digestion of the restriction enzyme site using an appropriate enzyme creates terminal sticky ends, which are used for DNA circularization of the target gene. The terminal nucleotide modification also introduces sequences encoding a backbone peptide linker upon DNA circularization. This is followed by treatment of a non-specific endonuclease optimized to introduce a single cut into the circular DNA construct. The result is linear permuted genes containing gaps and nicks that are later repaired by ligases and polymerases, creating blunt ended DNA (16). The resulting DNA construct is subsequently blunt-end ligated with a plasmid, as shown in FIG. 2. FIG. 2 is a schematic of circular permutation using restriction enzyme. Linear DNA with sticky ends is first cyclized, followed by treatment with restriction enzyme to create randomly cut linear DNA with nicks and gaps. Finally treatment with T4 DNA ligase and T4 DNA polymerase to repair nicks and gaps and create blunt ended circular permuted DNA. Though widely used, even this design improvement compared to rational design, has limitations—for example, optimizing conditions to introduce single cuts is technically difficult (17). In addition, random DNA cuts using a non-specific endonuclease such as DNase are sometimes difficult to control, and frequently result in truncations and duplications of parts of the DNA sequence (18-20). Furthermore, the blunt ended DNA that is generated after treatment with ligase is not preferred for ligation, as it may facilitate self ligation.

Alternatively, to mitigate the occurrence of truncations and duplications that occur when a non-specific endonuclease is used, one can employ a transposon for better control (21). While this method alleviates truncation and duplication, an unwanted 18 amino acids, resulting from DNA encoding the recognition binding sequences on the transposon, remained. Though proteins can sometimes tolerate additional amino acids appended to their C termini, these appendages usually serve a purpose—for example, purification. However, the additional sequence adds no value to the circularly permuted protein. The wide ranging use of transposons have been exhaustively reported elsewhere (21-25), and will not be elaborated on in this disclosure. However, recently, the present inventors also engineered a new transposon called MuST that facilitates facile construction of a random domain insertion library. The MuST transposon was designed with specific restriction sites at the 5' and 3' ends of the transposon, between the cleavage recognition sequence and the recognition binding site of the transposon, which allows for optimal control of composition and length of inter-domain linker residues (26). FIG. 11 shows wild type Mu Transposon with R1 and L1 recognition binding sites sequence. Blue arrows indicate Mu Transposon cleavage sites.

Accordingly, there is a need for new and different methods for designing circular permuted proteins. It is to this need and others that the present invention is directed.

BRIEF SUMMARY OF THE INVENTION

The present invention is generally related to the field of designing circular permuted proteins and is more specifically related to the field of designing circular permuted proteins using two engineered Mu transposons, MuCP-ISC (Mu Circular permutation transposon with Integrated Start Codon) and MuCP-ISSC (Mu Circular permutation transposon with Integrated Start and Stop Codon), for easy construction of random circular permuted proteins.

Previously reported was an engineered Mu transposon, MuST transposon, which facilitates random protein domain insertion with optimum linker length and composition. The MuST transposon was modified using polymerase chain reaction (PCR) to create the MuCP transposon. Specifically, in the present invention, we replaced a bcII site at the 5' end of the Mu transposon with an NdeI site, located inside of the TG recognition nucleotides. The NdeI restriction site for the MuCP transposon was designed in such a way to later serve as a start codon for the protein that will be circularly permuted. The AgeI restriction site at the 3' end of the MuST transposon remained unchanged in the MuCP transposon; this transposon is called MuCP-ISC. Another transposon, MuCP-ISSC, was made by replacing the AgeI site with an AflII site, which would later serve as a stop codon that terminates translation of the circular permuted protein.

Circular permutation is an important protein engineering tool used to create sequence diversity of a protein by changing its linear order of amino acid sequence. Circular permutation has proven to be effective in the evolution of proteins for desired properties while maintaining similar three-dimensional structures. Due to the lack of a robust design principle guiding the selection of new termini, construction of a combinatorial library is much preferred for comprehensive evaluation of circular permutation. The conventional methods used to create random circular permutation libraries cause significant sequence modification at new termini of circular permutants. In addition, the conventional methods impose additional limitations by requiring either relatively inefficient blunt-end ligation during library construction or redesign of transposons for tailored expression of circular permutants. The present invention provides for the development of an engineered transposon for facile construction of random circular permutation libraries. Minimal modification at the new termini of the random circular permutants is possible with the engineered transposon disclosed herein. In addition, the inventive method enables the use of sticky-end ligation during library construction and provides external tunability for expression of random circular perm utants.

The use of two engineered MuCP transposons allows for at least:

Optimal control of terminal backbone linker length;
Facilitation of sticky end ligation during construction of a random circular permutation protein libraries;
Restriction of the length of the N-terminus appended amino acids to 1 for both MuCP-ISSC and MuCP-ISC;
Restriction of the length of the C-terminus appended amino acids to 2 for MuCP-ISSC and 3 for MuCP-ISC;
Serving as excellent tools for making circular permuted proteins with known or unknown tertiary structure (all that is required is the primary sequence of the protein);
Eliminating truncations and minimizing duplications of the original proteins (preservation of primary sequence); and
Allowing easy shuttling of circular permuted libraries from one vector to another.

The present invention can be used use in industrial or research laboratories, when designing novel proteins for example for:

Increasing proteolytic or other stability;
Altering substrate specificity; and/or
Increasing allosteric interactions between coupled proteins.

These features, and other features and advantages of the present invention will become more apparent to those of ordinary skill in the relevant art when the following detailed description of the preferred embodiments is read in conjunction with the appended drawings.

BRIEF DESCRIPTIONS OF THE DRAWINGS

FIG. 1 represents a Transposon design for A: MuCP-ISC at the 3' end AgeI and CA recognition cleavage sequence and B: MuCP-ISSC, at the 3' end AflII and CA recognition sequence. Each transposon has at the 5' end an NdeI site, preceded by TG cleavage recognition sequence.

FIG. 2 is a schematic of prior art circular permutation using restriction enzyme. Linear DNA with sticky ends is first cyclized, followed by treatment with restriction enzyme to create randomly cut linear DNA with nicks and gaps. Finally treatment with T4 DNA ligase and T4 DNA polymerase to repair nicks and gaps and create blunt ended circular permuted DNA.

Figure 6:
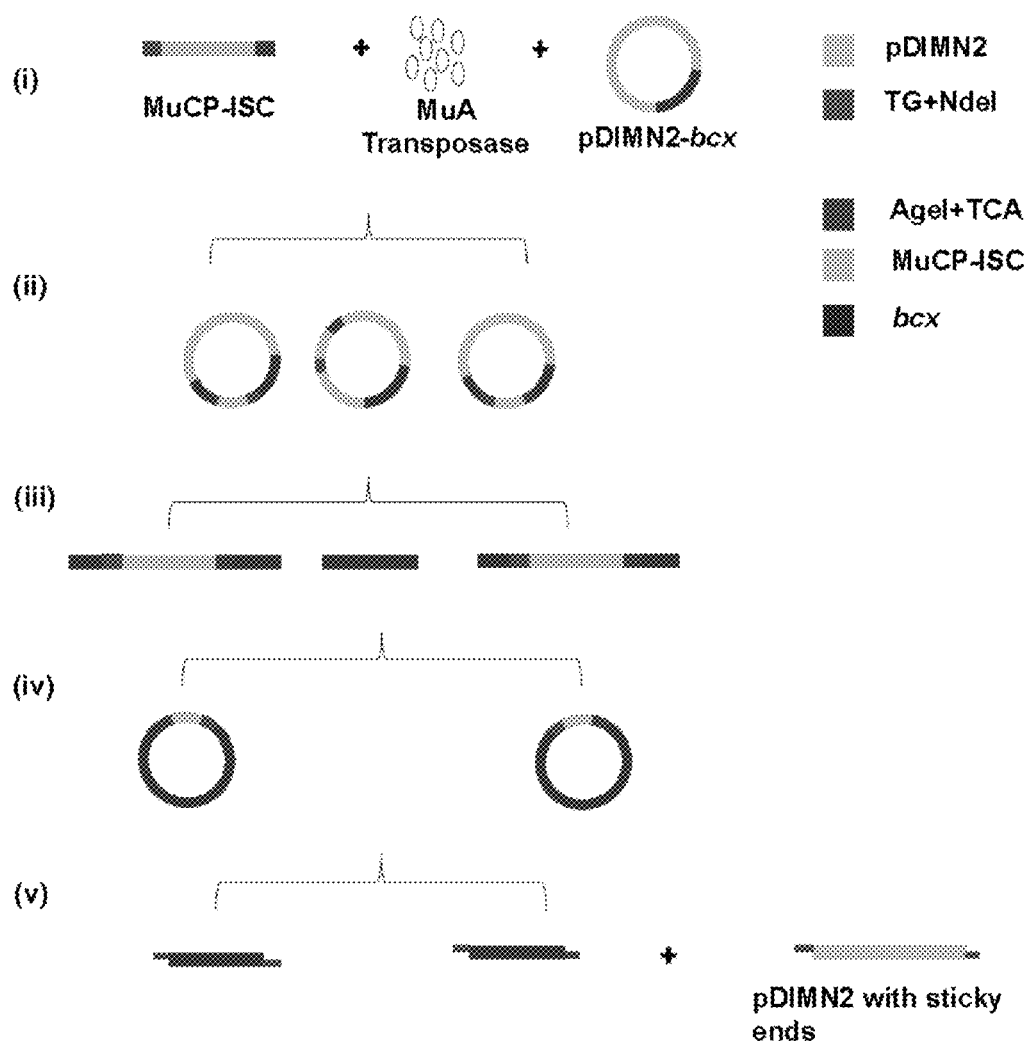

FIG. 6 represents (i) MuCP-ISC transposon is mixed with MuA transposase and pDMIN2-bcx; (ii) randomly inserted library of pDMIN2-bcx-MuCP-ISC; (iii) digestion with SpeI to create sticky ended bcx-MuCP-ISC; (iv) self ligation to create cyclized bcx-MuCP-ISC; (v) cyclized bcx-MuCP-ISC is digested with NdeI and AgeI to form sticky ends and MuCP-ISC removed. A library of random circular permuted linear bcx is ready for ligation to a vector with corresponding restriction sites.

Figure 7A:
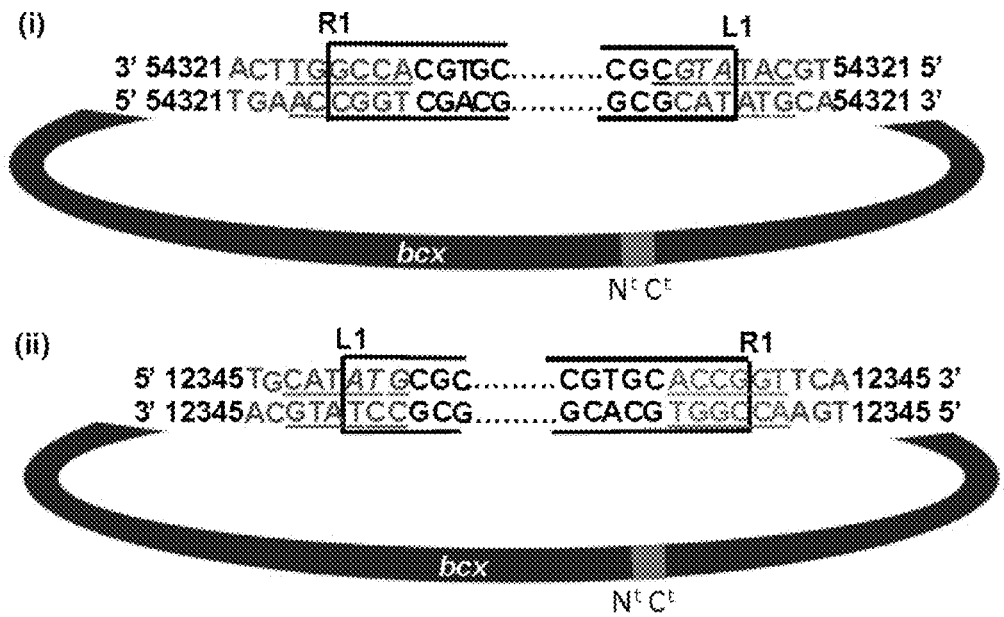
Figure 7B:
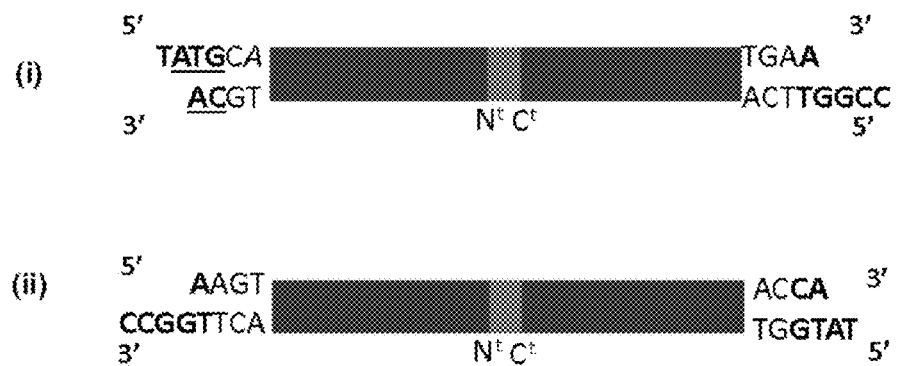

FIG. 7A represents (i) MuCP-ISC transposon inserted in the 3' to 5' position into the bcx and (ii) MuCP-ISC transposon inserted in the 5' to 3' position into the bcx (SEQ ID NOS 24-27, 25, 24 and 28-29, respectively, in order of appearance). FIG. 7B represents (i) circularly permuted bcx with NdeI and incorporated ATG start codon and (ii) circularly permuted bcx in nonfunctional configuration. $N^t$ and $C^t$ represent the old N and C termini.

Figure 8A:
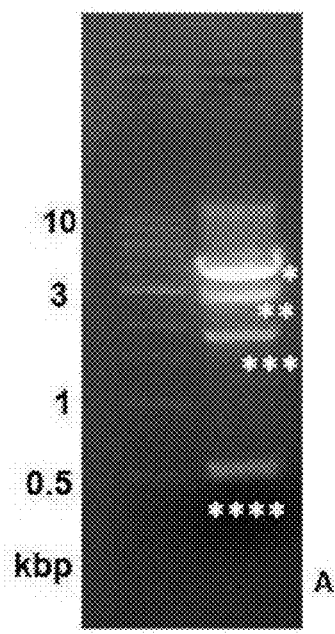
Figure 8B:
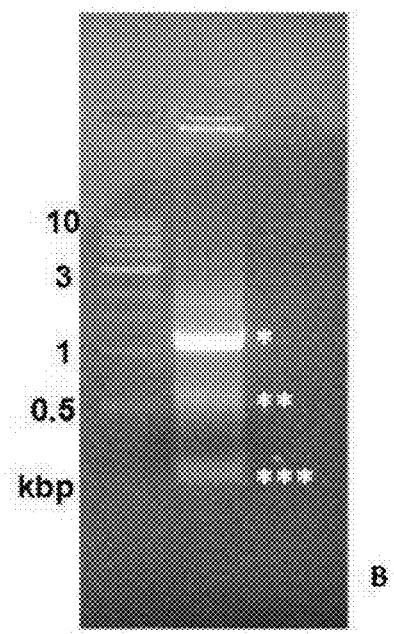

FIG. 8A represents an agarose gel electrophoresis analysis in which digestion with SpeI restriction enzyme results in randomly inserted MuCP-ISC transposon into the plasmid pDIMN2-bcx. The band correspond to ~1850 bp size (***) represents MuCP-ISC transposon inserted into target gene bcx, which was excised and gel purified. In FIG. 8A *,  and ** represent MuCP-ISC transposon+pDIMN2, pDIMN2 and bcx, respectively. FIG. 8B represents an agrose gel electrophoresis analysis showing excision of MuCP-ISC transposon by double digestion of self-ligated randomly inserted MuCP-ISC transposon+bcx with NdeI and AgeI restriction enzymes. In FIG. 8B *,  and * represent partial MuCP-ISC transposon, circularly permutated bcx and the rest of the MuCP-ISC transposon.

Figure 9A:
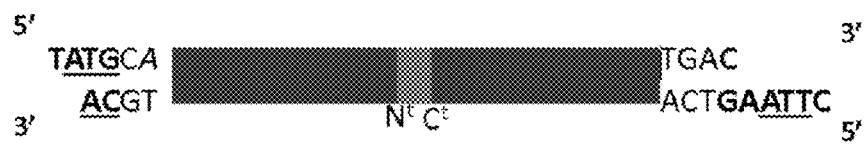
Figure 9B:
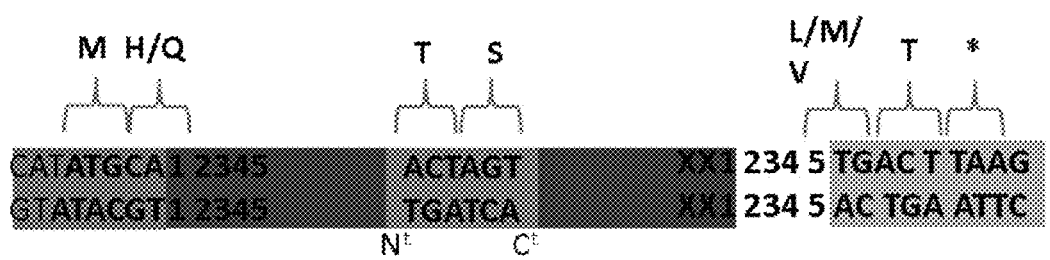

FIG. 9A represents the MuCP-ISC transposon inserted in the 3' to 5' position into the bcx. bcx has NdeI and incorporated ATG start codon and AflIII TAA (or reverse complement ATT) stop codon. FIG. 9B is a schematic where MuCP-ISSC produces an H or Q and (L or M or V)-T are generated at the N and C termini, respectively. A T-S linker forms at the N and C termini.

Figure 10:
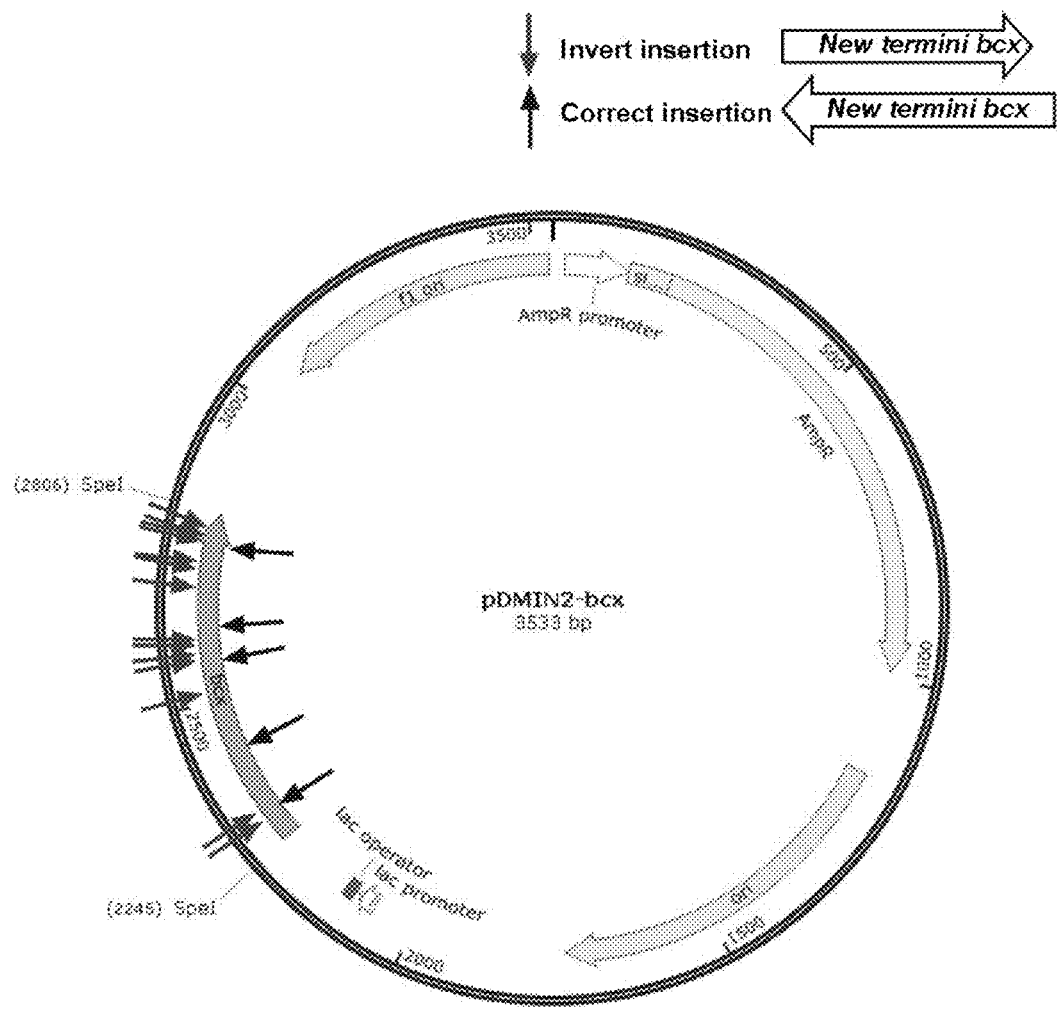

FIG. 10 is a vector map showing library of random circularly permuted bcx. Red arrows show inserted transposons in the orientation leading to functional variants, and blue arrows show transposons inserted in the orientation leading to nonfunctional variants.

Figure 11:
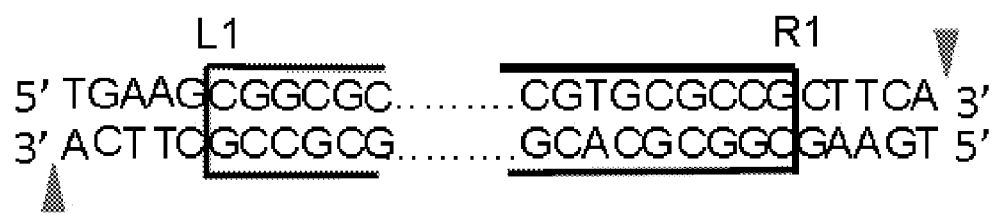

FIG. 11 represents Wild type Mu Transposon with R1 and L1 recognition binding sites sequence (SEQ ID NOS 30-33, respectively, in order of appearance). Blue arrows indicate Mu Transposon cleavage sites

DETAILED DESCRIPTION OF PREFERRED EMBODIMENTS

In the present invention, the design of two engineered Mu transposons is described, MuCP-ISC (Mu Circular permutation transposon with Integrated Start Codon) and MuCP-ISSC (Mu Circular permutation transposon with Integrated Start and Stop Codon), for easy construction of random circular permuted proteins. Two engineered MuCP transposons allow for optimal control of terminal backbone linker length, and facilitates sticky end ligation during construction of a random circular permutation library. The method also restricts the length of the appended amino acids to 1 at N-terminus for both MuCP-ISSC and MuCP-ISC and to 2 and 3 at C-terminus for MuCP-ISSC and MuCP-ISC, respectively. The length of the linker sequence connecting the N and C termini is flexible.

Materials and Methods

Two Mu transposons containing i) the chloramphenicol resistance (Cm) gene and ii) the kanamycin resistance (KmR) gene and MuA transposase, Dharmacon products (Lafayette, Colo., USA) were used as a starting point for the creation of all future transposon variants. Bioassay dishes were purchased from Thermo Fisher Scientific (Rochester, N.Y., USA). High fidelity platinum Pfx DNA polymerase was used to carry out all PCR reactions and DH5α cells were obtained from Life technologies (Carlsbad, Calif., USA). All DNA purification kits and columns were obtained from Zymo Research Corporation (Irvine, Calif., USA). T4 DNA ligase and all other restriction enzymes were products of New England Biolabs, Inc. (Ipswich, Mass., USA).

Preparation of an MuCP for Random Circular Permutation

Figure 1:
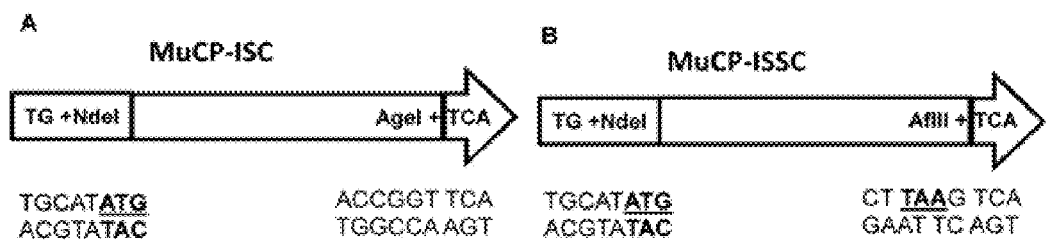
Figure 2:
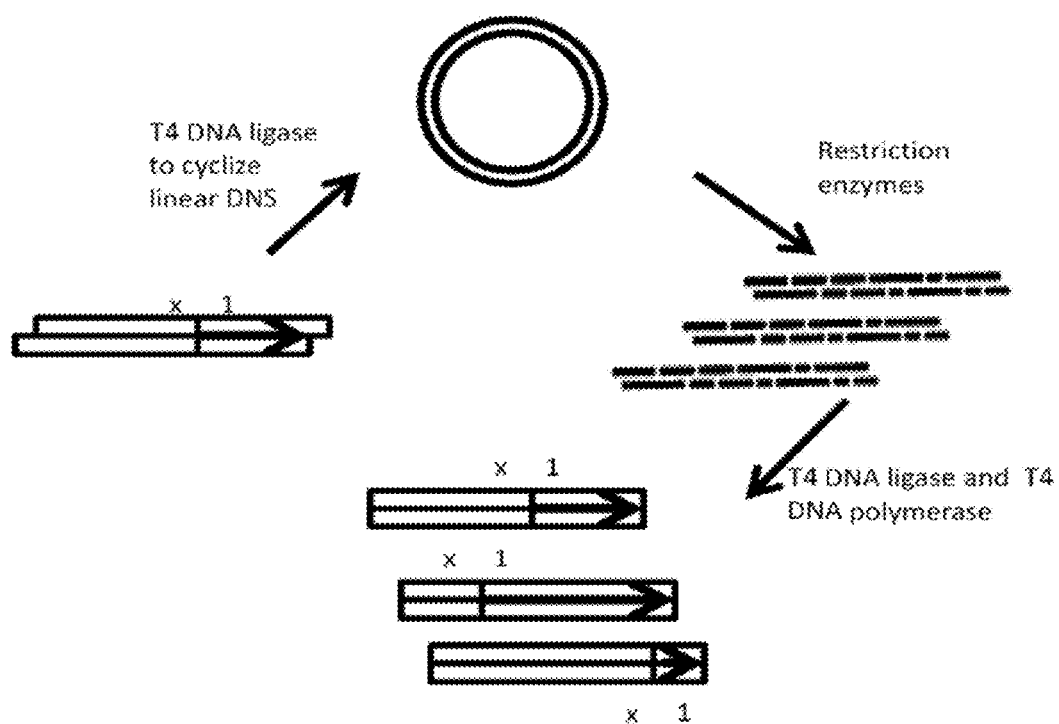

FIG. 1 represents the transposon design for A: MuCP-ISC at the 3' end AgeI and CA recognition cleavage sequence and B: MuCP-ISSC, at the 3' end AflIII and CA recognition sequence. Each transposon has at the 5' end an NdeI site, preceded by TG cleavage recognition sequence.

Figure 5:
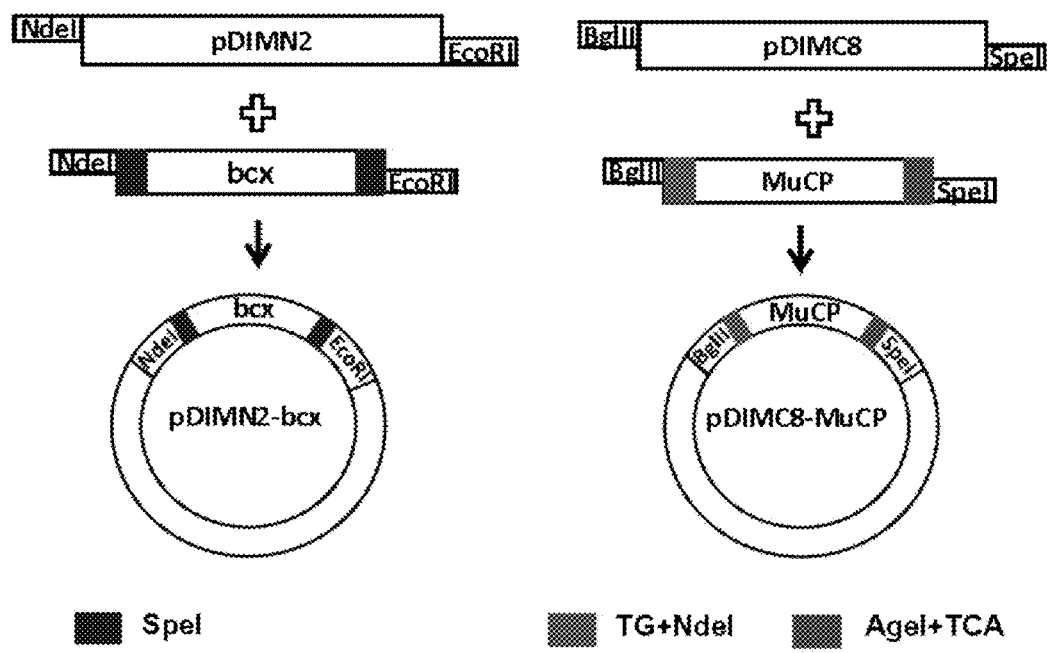
FIG. 5 show on the left the assembly of pDIMN2-bcx and on the right the assembly of pDIMC8-MuCP.

Previously reported was an engineered Mu transposon, MuST transposon, which facilitates random protein domain insertion with optimum linker length and composition (26). The MuST transposon was modified using PCR to create the MuCP transposon. Specifically, we replaced a BclI site at the 5' end of the Mu transposon with an NdeI site, located inside of the TG recognition nucleotides. The NdeI restriction site for the MuCP transposon was designed in such a way to later serve as a start codon for the circularly permuted bcx. The AgeI restriction site at the 3' end of the MuST transposon remained unchanged in the MuCP-ISC transposon. A BgIII restriction site was placed upstream of the NdeI site, at the 5' end, before the TG recognition site. And downstream of the AgeI site at the 3' end, after the CA recognition site, an SpeI restriction site was added to the MuCP transposon to facilitate its ligation to pDIMC8 (FIG. 5). Unique restriction sites were used for easy sticky end ligation into the host vector, which also allowed for scale up of the MuCP transposon through simple cell growth, purification and subsequent digestion.

Preparation of the pDIMN2-bcx Plasmid

Referring to FIG. 5, conventional PCR techniques were used to append NdeI and EcoRI restriction sites at the 5' and 3' ends of a pDIMN2 vector containing the gene sequence coding for alpha synuclein, to create linearized pDIMN2. Also, for the target insert sequence, Xylanase from *Bacillus Circulans* (bcx), the same two restriction sites which facilitate ligation between the vector and the insert, were appended at the 5' and 3' ends using PCR. At the 5' end of the target insert gene, a SpeI restriction site was placed downstream to the NdeI restriction site, before the sequence encoding bcx. Another SpeI restriction site was placed upstream to the EcoRI restriction site, at the 3' end of the sequence encoding bcx. These dual SpeI sites of the insert target gene were later used to encode a Thr-Ser amino acid linker that connects the original N and C termini of the BCX.

The PCR products for the vector and the target gene were then purified using Zymo Research gel extraction kit, followed by digestion with NdeI and EcoRI restriction enzymes to generate sticky-ends. After purification, the digested bcx gene was ligated with the digested pDIMN2 vector using 400 units of T4 DNA ligase. The ligation mixture was purified by ethanol precipitation and subsequently transformed into DH5α by electroporation at 2000 V using a Bio-Rad Gene Pulser. The electroporated cells were then incubated in Super Optimal Broth containing glucose (SOC) media at 37° C. for 1 hour with constant shaking at 250 rpm in a New Brunswick Scientific Innova TM4230 incubator. The electroporated cells were subsequently plated on LB-agar plates supplemented with 100 ug/ml of Ampicillin (amp) and incubated for 16-24 hour at 37° C. Selected colonies were re-grown and the plasmids were subsequently extracted using the Zymo plasmid miniprep kits. The plasmids were then sequenced at Genewiz, Inc (South Plainfield, N.J., USA).

Preparation of pDIMC8-MuCP-ISC Plasmid

PCR was carried out on pDIMC8-MalE (27) to produce a linearized pDIMC8 with EcoR1 restriction site at the 3' end and an Nde1 restriction site at the 5' end that will later connect to the 5' end and 3' end respectively, of the MuCP-ISC transposon. The PCR product for the MuCP-ISC transposon of (1300 bp) and pDIMC8 vector with modified ends (4500 bp) were separated by agarose gel electrophoresis and purified using the Zymo plasmid miniprep kit. The pDIMC8 vector was used for replication of the transposon sequence, making the pDIMC8-MuCP-ISC transposons. The purified PCR products were digested using BgIII and SpeI restriction enzymes, then purified using the Zymo gel extraction kit. Using the manufacturer's recommendation of T4 DNA ligase, the digested MuCP-ISC transposon was then ligated to pDIMC8 to make the complete pDIMC8-MuCP-ISC plasmid. Then the ligation mixture was purified by ethanol precipitation and subsequently transformed into DH5α, by electroporation at 2000 V using a Bio-Rad Gene Pulser. The electroporated cells were then incubated in SOC media at 37° C. for 1 hour with constant shaking at 250 rpm to enable cell repair. Afterwards the electroporated cells were plated on LB-agar plates supplemented with 50 μg/ml of Chloramphenicol and incubated for 16-24 hours at 37° C. Selected colonies were re-grown in 10 ml LB cultures overnight at 37° C., after which the plasmids were extracted using the Zymo plasmid miniprep kits. Plasm ids were sequenced at Genewiz, Inc (South Plainfield, N.J., USA) and the cells containing the correct sequence of MuCP-ISC transposons were stored in 25% glycerol at −75° C.

Preparation of pDIMC8-MuCP-ISSC Plasmid

Another transposon was designed, where an AflIII site replaced the AgeI site in order to facilitate termination of translation of the final circular permuted protein sequence, without making modifications to the host plasmid vector. This alternative transposon, was constructed using the same procedure for the MuCP-ISC.

Random Insertion of the MuCP-ISC Transposon into pDIMN2-Bcx

The transposition reaction was carried out with 20 ng of the MuCP-ISC transposon, 160 ng of the target DNA (i.e., pDIMN2-bcx) and 22 ng of MuA transposase in 1× reaction buffer (25 mM Tris HCl, 10 mM MgCl2, 0.05% Triton X-100 and 10% glycerol at pH 8.0) in a total volume of 20 µl at 30° C. The transposition reaction mixture was incubated for 1 hour at 30° C. MuA transposase was then heat-inactivated at 65° C. for 15 minutes to stop the transposition reaction. Aliquots (0.5 µl) of transposition reaction mixture was then transformed into 50 µl of DH5α by electroporation at 1700 V using a Bio-Rad Gene Pulser (Hercules, Calif., USA). The electroporated cells were then incubated in SOC media at 37° C. for 1 hour with constant shaking at 250 rpm. Five percent of recovered cells were plated on small LB-agar plates supplemented with 50 µg/ml of chloramphenicol (Cm) and 100 µg/ml of ampicillin (Amp). Colonies grown on these plates during overnight incubation at 37° C. were counted in order to calculate the transposition efficiency (i.e., the number of colonies grown on the Amp/Cm plates after transformation with 0.5 µl of the transposition mixture). Note that the $Cm^R$ gene was included in the MuCP-ISC transposon, but not the pDIMN2 which contained the $Amp^R$ gene. As such, only colonies harboring pDIMN2-bcx with the inserted MuCP-ISC transposon were able to grow on $Amp^R/Cm^R$ plates. The recovered cells were also plated on large $Amp^R/Cm^R$ plates, followed by overnight incubation at 37° C. Colonies grown on these plates were collected by adding 4×15 ml storage media (36 ml of LB, 18 ml of 50% glycerol and 6 ml of 20% (w/v) glucose) at the top of the each plate followed by the transfer of cell suspension into polypropylene centrifuge tubes. Next, the cell suspension was centrifuged at 5000 rpm at 4° C. for 10 minutes and supernatant was decanted. The plasmids with the randomly inserted transposons were then extracted en masse using the Zymo plasmid midiprep kit.

Digestion of MuCP-ISC inserted into the pDIMN2-bcx was carried out with SpeI restriction enzyme at 37° C., followed by heat inactivation of restriction enzyme at 65° C. for 15 min. The digested DNA was then separated by gel electrophoresis. The appropriate band of ~1850 bp in size resulting from transposition of the MuCP-ISC transposon (1300 bp) into the bcx gene (~550 bp) was extracted and gel purified using the Zymo plasmid miniprep kit. The purified recombined DNA was then digested with SpeI to create sticky 5' and 3' ends, and subsequently circularized by self-ligation using the manufacturers recommendation of T4 DNA ligase. After purification of the ligated mixture using Zymo plasmid miniprep kit, another digestion with NdeI and AgeI was performed on the circularized DNA of randomly inserted MuCP-ISC transposon at 37° C., followed by heat inactivation of restriction enzyme at 65° C. for 15 minutes. The resulting randomly circularly permuted bcx gene (~550 bp) was excised by gel electrophoresis and gel purified using the Zymo plasmid miniprep kit. Random circularly permutated bcx gene with generated sticky-ends was then ligated with the host pDIMN2 vector using 400 units of T4 ligase. DNA precipitation, transformation, cell growth and DNA extraction of selected colonies were then carried out as previously mentioned and sent to Genewiz for sequencing.

Results

FIG. 6 represents (i) MuCP-ISC transposon is mixed with MuA transposase and pDMIN2-bcx; (ii) Randomly inserted library of pDMIN2-bcx-MuCP-ISC; (iii) Digestion with SpeI to create sticky ended bcx-MuCP-ISC; (iv) Self ligation of bcx to create cyclized bcx; and (v) Cyclized bcx-MuCP-ISC is digested with NdeI and AgeI to form sticky ends. A library of random circular permuted linear bcx is ready for ligation to a vector with corresponding restriction sites.

Random Circular Permutation

Transposons can be powerful tools in protein engineering. Presently, there are a large number of commercially available transposons, as well as numerous devised transposon facilitated techniques—all serving a variety of purposes (21, 28, 29). The two transposons presented in this disclosure are modifications to the existing MuST transposon, previously created in the present inventors' lab. The two designed transposons, MuCP-ISC (Mu Circular permutation transposon with Integrated Start Codon) and MuCP-ISSC (Mu Circular permutation transposon with Integrated Start and Stop Codon), each contained unique restriction sites that would later serve to create sticky ended circular permuted DNA of bcx that ligates to a host vector pDIMN2. The unique restriction sites also serves as start and stop codons, allowing for initiation and termination of translation of the circular permuted protein. A summary of the method is illustrated in FIG. 6. For brevity, the transposon forms a complex with the MuA transposase called the transposome (30), which then inserts the transposon throughout the target plasmid containing bcx. After, the target DNA is added and the transposition mixture transformed into bacterial cells. To ensure proper selection of colonies containing only the bcx with inserted transposon, different antibiotic restriction genes were added to the transposon and the host vector containing the bcx, so when exposed to both antibiotics, only colonies with the necessary antibiotic resistance genes can survive. Following the selection of viable colonies, the random DNA comprising transposon inserted in bcx is extracted, then digested with appropriate restriction enzymes to yield only the linear version of the bcx-MuCP. This linear DNA is then cyclized by self-ligation, and subsequently digested, leaving the random circular permuted bcx. The random circularly permuted bcx is finally ligated to a desired host vector with similar corresponding restriction sites and expressed in the cell line of choice.

Design of MuCP-ISC

FIG. 7A represents (i) MuCP-ISC transposon inserted in the 3' to 5' position into the bcx and (ii) MuCP-ISC transposon inserted in the 5' to 3' position into the bcx. FIG. 7B represents (i) bcx with NdeI and incorporated ATG start codon and (ii) bcx in nonfunctional conformation. $N^t$ and $C^t$ represent the old N and C termini.

Mutations used to create the NdeI and AgeI restriction sites are made between the region of wild type Mu transposon cleavage site and the MuA transposase recognition binding sites (see FIG. 11), therefore compromising the transposon to the extent of inoperability is unlikely (26,31). Not to be overlooked is the orientation in which the transposon is inserted. When the transposon is inserted in a 3' to 5' manner into a 5' to 3' orientation for bcx, there will be functional expression of the bcx as long as insertion occurs in the correct frame (FIGS. 7A(i) and 7B(i)). Whereas 5' to 3' insertion of the transposon into 5' to 3' for bcx results in non-functional expression (FIGS. 7A(ii) and 7B(ii)). Functional expression of circular permutated bcx is possible when circularly permutated bcx is in-frame to additional residues located at the new C-terminus (e.g., Leu/Met/Val, Asn, Arg).

Figure 3:
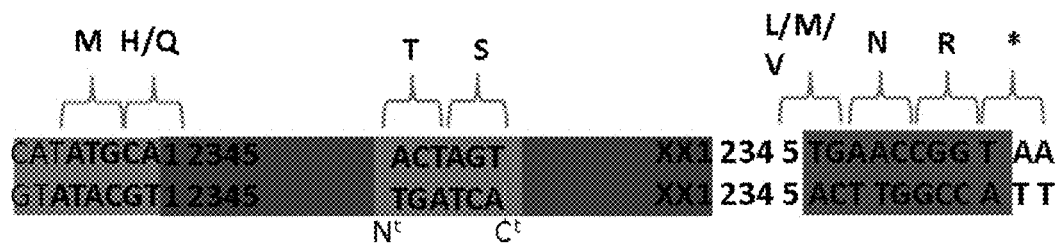
FIG. 3 is a schematic where MuCP-ISC produces an H or Q and (L or M or V)—N—R at the N and C termini, respectively. $N^t$ and $C^t$ represents the old N and C termini join to form a T-S linker (SEQ ID NOS 22-23, respectively, in order of appearance).
Figure 4:
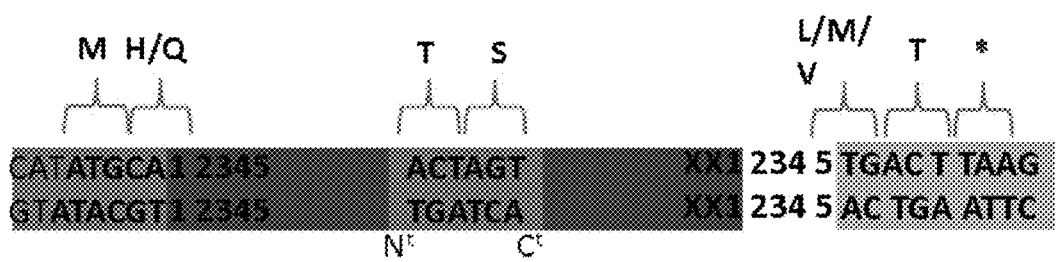
FIG. 4 is a schematic where MuCP-ISSC produces an H or Q and (L or M or V)-T are generated at the N and C termini, respectively. A T-S linker forms at the old N and C termini.

Referring to FIG. 3, the well positioned sticky end restriction sites also aid in preventing unnecessary appended amino acids that are non-native to the final product. Depending on the nucleotide involved at the insertion site, at the N terminus, either a His or a Gln can be present, preceded by the start codon, Met. Close to the 5' end there is a 5 bp duplicated sequence which is also generated—an inherent feature of transposition (24). For MuCP-ISC, these five repeated base pairs, contingent on insertion location, encode for one repeated amino acid of the target protein and Leu or Met or Val, followed by an Asn and an Arg. The Asn and Arg are generated from the AgeI site placed at the 3' end upon reversed insertion in combination with the AA nucleotide sequence derived from the host vector, which constitute the stop codon. Ligation of the two SpeI sites originally placed at the 5' and 3' ends lead to a short T-S linker. However, if necessary, this linker length may be increased and varied by genetically modifying the region between the SpeI sites and the bcx. FIG. 3 is a schematic where MuCP-ISC produces an H or Q and (L or M or V)—N—R at the N and C termini, respectively. $N^t$ and $C^t$ represents the old N and C termini join to form a T-S linker.

Selection of Randomly Inserted MuCP-ISC Transposon into Bcx and Randomly Permuted Bcx The transposition efficiency of MuCP-ISC, in CFU (Colony Forming Units) was $1.1 \times 10^4$/ug or ng DNA used. A 1.25 fold drop in efficiency compared to the original MuST transposon and 7.5 fold compared to the wild type Mu transposon. Even though the transposon's transposition efficiency was reduced, it still produced sufficient number of randomly inserted pDMIN2-bcx-MuCP-ISC statistically necessary to explore circular permutation of the entire ~555 bp bcx. After collection of the random transposition library members, the plasmids were extracted en masse and the SpeI restriction sites, which were placed at the 5' and 3' ends of bcx to create sticky ends for self-ligation, were digested with SpeI restriction enzyme. A band of ~1850 bp, indicating insertion of the ~1300 bp MuCP-ISC transposon into the ~555 bp bcx was then isolated from the gel (FIG. 8A).

FIG. 8A represents an agarose gel electrophoresis analysis in which digestion with SpeI restriction enzyme, which results in randomly inserted MuCP-ISC transposon into the plasmid pDIMN2-bcx. The band correspond to ~1850 bp size (***) represents MuCP-ISC transposon inserted into target gene bcx, which was excised and gel purified. In FIG. 8A *,  and ** represent MuCP-ISC transposon+pDIMN2, pDIMN2 and bcx, respectively. FIG. 8B represents an agarose gel electrophoresis analysis showing excision of MuCP-ISC transposon by double digestion of self-ligated randomly inserted MuCP-ISC transposon+bcx with NdeI and AgeI restriction enzymes. In FIG. 8B *,  and * represent partial MuCP-ISC transposon, circularly permutated bcx and the rest of the MuCP-ISC transposon.

The isolated DNA fragments were circularized through self-ligation using T4 DNA ligase (via the SpeI restriction sites located at the original 5' and 3' ends of bcx) followed by gel purification. Subsequent double digestion of the circularized DNA (excision of transposon) with the NdeI and AgeI restriction enzymes produced a band of ~580 bp, corresponding to circularly permuted bcx (FIG. 8B). The ~580 bp random circular permuted DNA was ligated to the host pDIMN2 vector to produce a diverse library of pDIMN2-cp-bcx (circular permuted bcx in pDMIN2) pDIMN2 containing circular permuted bcx). We did not screen potential viable candidates for activity at the protein level, instead, as a proof of concept, we extracted DNA from randomly chosen colonies and performed DNA sequencing to detect successful outcomes.

A similar procedure for MuCP-ISSC was followed, and again colonies of randomly inserted transposon into bcx were present, though transposon efficiency was significantly compromised. No extensive optimization of the transposition reaction was carried out. FIG. 9A shows details of the MuCP-ISSC transposon. In the case of MuCP-ISSC, part of the AflIII site acts as a built-in stop codon with the remainder coding for Leu or Met or Val and Thr at the C terminus (FIG. 9B).

FIG. 9A represents the MuCP-ISC transposon inserted in the 3' to 5' position into the bcx. Circularly permuted bcx has NdeI and incorporated ATG start codon and AflIII TAA (or reverse complement ATT) stop codon. FIG. 9B is a schematic where MuCP-ISSC produces an H or Q and (L or M or V)-T are generated at the N and C termini, respectively. A T-S linker forms at the old N and C termini.

The vector map (FIG. 10) of pDIMN2-bcx and Table 1 shows the randomness in the selected circular permuted variants. Twenty one colonies were sequenced and two contained in frame, correctly inserted bcx. This result is in approximate agreement with the statistical possibility of having one successful permutation of the six possibilities, also previously reported (21).

FIG. 10 is a vector map showing library of random circularly permuted bcx. Red arrows show inserted transposons in the orientation leading to functional variants, and blue arrows show transposons inserted in the orientation leading to nonfunctional variants. Table 1 represents the exact by transposon insertion sites for MuCP-ISC transposon.

TABLE 1

Representative nucleotide sequences of randomly circularly permuted bcx obtained from a library constructed in this study
Sequences (SEQ ID NOS 1-4, 2, 5-6, 2, 7-8, 2, 9-10, 2, 11-12, 2, 13-14, 2, 15-16, 2, 17-18, 2, 19-20, 2 and 21 respectively, in order of appearance)

ATGCA $^{41}$GTATC...TGG$^{555}$ ACTAGT $^{1}$GCC...GTATC$^{45}$ TGAACCGGTAA

ATGCA $^{58}$AACGG...TGG$^{555}$ ACTAGT $^{1}$GCC...AACGG$^{82}$ TGAACCGGTAA

ATGCA $^{64}$TCCGG...TGG$^{555}$ ACTAGT $^{1}$GCC...TCCGG$^{88}$ TGAACCGGTAA

TABLE 1-continued

Representative nucleotide sequences of randomly circularly permuted bcx obtained from a library constructed in this study
Sequences (SEQ ID NOS 1-4, 2, 5-6, 2, 7-8, 2, 9-10, 2, 11-12, 2, 13-14, 2, 15-16, 2, 17-18, 2, 19-20, 2 and 21 respectively, in order of appearance)

*ATGCA* $^{138}$CCCGT...TGG$^{555}$ *ACTAGT* $^{1}$GCC...CCCGT$^{142}$ *TGAACCGGTAA*

*ATGCA* $^{195}$CCTGA...TGG$^{555}$ *ACTAGT* $^{1}$GCC...CCTGA$^{199}$ *TGAACCGGTAA*

*ATGCA* $^{221}$CGCCA...TGG$^{555}$ *ACTAGT* $^{1}$GCC...CGCCA$^{225}$ *TGAACCGGTAA*

*ATGCA* $^{288}$CGACT...TGG$^{555}$ *ACTAGT* $^{1}$GCC...CGACT$^{273}$ *TGAACCGGTAA*

*ATGCA* $^{334}$AGATA...TGG$^{555}$ *ACTAGT* $^{1}$GCC...AGATA$^{338}$ *TGAACCGGTAA*

*ATGCA* $^{387}$ACCAC...TGG$^{555}$ *ACTAGT* $^{1}$GCC...ACCAC$^{371}$ *TGAACCGGTAA*

*ATGCA* $^{451}$AATGC...TGG$^{555}$ *ACTAGT* $^{1}$GCC...AATGC$^{455}$ *TGAACCGGTAA*

The bold letters represent sequences derived from bcx. The numbers next to bold letters indicate nucleotide number of bcx. The italic letters, ATGCA is derived from the reverse complement of part of the TG + NdeI sequence, ACTAGT from SpeI and TGAACCGGT is derived from the reverse complement of the AgeI + TCA sequence. The other plain letters, AA, are derived from pDIMN2.

Discussion

The robustness and efficacy of the present method hinges on two key design features. First, using lessons learned from the use of DNAse restriction enzymes and previous transposon mutagenesis, unique restriction sites were incorporated into the composition of the transposon. By doing so, the randomness of transposition while having the ability to precisely remove the inserted transposon. At the same time, the incorporated restriction enzyme sites served for sticky end ligation, eliminating the need for additional repair of nicks and gaps, which is typical in DNAse-mediated random circular permutation. Second, the integrated transposon restriction sites, further downstream of the present process, serve as or comprise part of a start and stop codon that terminates translation. To the inventors' knowledge, no other transposon with integrated start and stop features have been reported. The engineered sequence between transposase recognition bindings sites and the transposon cleavage sites plays the crucial role of reducing the number of amino acids appended to the new C-term inus of the circularly permutated proteins, down to two or three, dependent on the transposon used, compared to 18 in previous studies (21). The present method also prevents ill-effects produced from uncontrolled digestion of target DNA, which means no unexpected duplication and truncation of structural features, which may range anywhere from −48 to +16 (18). Too great a change in the primary sequence of the circularly permuted protein could significantly disturb the folding properties and hence, stability of the circular permuted protein. Except for the start codon, Met (usually removed (32)), only one additional amino acid was attached to the N-terminus of randomly circularly permuted proteins, preserving as much as possible the native primary sequence. Furthermore, with the recent interest in domain insertion of circularly permuted proteins into host proteins (33), the two engineered transposons has potential to be highly effective due to the minimal change in primary structure of the native protein.

The design of MuCP-ISSC and MuCP-ISC does not need to be altered based on the target protein, unlike the other available method, where separate antibiotic resistance of the transposon and the target DNA are tied together and necessary for not only the selection of variants, but also for their generation (21). The necessity to couple transposon and target DNA means a new transposon has to be designed for every new circular permuted protein—limiting the general applicability of the method. It is true that MuCP-ISSC and MuCP-ISC also use multiple antibiotic resistant genes for efficient selection of viable colonies, but it is not necessary as an independent expression system with appropriate resistant gene can be incorporated into the MuCP-ISSC and MuCP-ISC transposons to allow for expression, while using a pre-circularized target DNA without an antibiotic resistant gene, similar to that used in other methods using DNAseI (34). Once the modified MuCP with built in expression features is inserted into the target DNA, additional steps in obtaining linear randomly permuted DNA can be carried out as described in this disclosure. The MuCP assisted method also offers easy removal of the inserted transposon by way of restriction enzymes, to create sticky ends on the circular permuted target DNA, making it easy to shuttle the circular permuted library that will later be cloned into different vectors—all without redesigning the MuCP transposon, as long as the vectors contain compatible restriction sites for ligation.

Thus, embodiments of the invention include a method for designing circular permuted proteins, comprising constructing random circular permuted proteins using two engineered Mu transposons. In this method, at least one of the Mu transposons has an NdeI site at the 5' end of the Mu transposon and (a) an AgeI restriction site at the 3' end of the Mu transposon or (b) an AflII site at the 3' end of the Mu transposon. Additionally, the NdeI site is located inside of the TG recognition nucleotides, the NdeI site serves as a start codon for the protein that will be circularly permuted, and the AflII site serves as a stop codon that terminates translation of the circular permuted protein. Further, each of the transposons contains unique restriction sites that serve to create sticky ended circular permuted DNA that ligates to a host vector.

In other embodiments of the invention, each of the transposons contains unique restriction sites that serve to create sticky ended circular permuted DNA of *Bacillus Circulans* (bcx) that ligates to a host vector pDIMN2. The two engineered Mu transposons are Mu Circular permutation transposon with Integrated Start Codon (MuCP-ISC) and Mu Circular permutation transposon with Integrated Start and Stop Codon (MuCP-ISSC). This embodiment comprises restricting the length of the appended amino acids to 1 at N-terminus for both MuCP-ISSC and MuCP-ISC and to 2 and 3 at C-terminus for MuCP-ISSC and MuCP-ISC, respectively, and gives flexibility to the length of the linker sequence connecting the N and C termini. The transposon forms a complex with MuA transposase called the transposome, which then inserts itself into the target bcx. The restriction sites serve for sticky end ligation.

In additional embodiments of the invention, integrated transposon restriction sites, further downstream of the process, serve as or comprise part of a start and stop codon that terminates translation. The MuCP is not included in the circular permuted protein. The design of MuCP-ISSC and MuCP-ISC does not need to be altered based on the target protein.

Another embodiment of the invention is a method for designing circular permuted proteins, comprising (a) constructing random circular permuted proteins using a Mu Circular permutation transposon (MuCP); (b) restricting the length of the appended amino acids to 1 at N-terminus for the MuCP and to 2 or 3 at C-terminus for the MuCP; and (c) comprising giving flexibility to the length of the linker sequence connecting the N and C termini for the MuCP.

The MuCP is selected from the group consisting of Mu Circular permutation transposon with Integrated Start Codon (MuCP-ISC) and Mu Circular permutation transposon with Integrated Start and Stop Codon (MuCP-ISSC). Each of the MuCPs contains unique restriction sites that serve to create sticky ended circular permuted DNA of *Bacillus Circulans* (bcx) that ligates to a host vector pDIMN2. This embodiment can further comprise restricting the length of the appended amino acids to 1 at N-terminus for both MuCP-ISSC and MuCP-ISC and to 2 and 3 at C-terminus for MuCP-ISSC and MuCP-ISC, respectively, and giving flexibility to the length of the linker sequence connecting the N and C termini.

In other embodiments, (a) the MuCP-ISC is constructed by replacing a bcII site at the 5' end of the Mu transposon with an NdeI site, located inside of the TG recognition nucleotides, wherein the NdeI restriction site for the MuCP transposon serves as a start codon for the protein that will be circularly permuted, and wherein the AgeI restriction site at the 3' end of the Mu transposon remains unchanged; and (b) the MuCP-ISSC is constructed by replacing a bcII site at the 5' end of the Mu transposon with an NdeI site, located inside of the TG recognition nucleotides, wherein the NdeI restriction site for the MuCP transposon serves as a start codon for the protein that will be circularly permuted, and replacing the AgeI restriction site at the 3' end of the Mu transposon with an AflIII site, which serves as a stop codon that terminates translation of the circular permuted protein.

In further embodiments, (a) the MuCP is mixed with MuA transposase and pDMIN2-bcx and subjected to digestion with SpeI to create sticky ended bcx-MuCP-ISC; (b) the sticky ended bcx-MuCP is subjected to self ligation to create cyclized bcx-MuCP; and (c) the cyclized bcx-MuCP is digested with NdeI and AgeI to form sticky ends and the MuCP removed. In additional embodiments, (a) the MuCP is inserted in the 3' to 5' position into the bcx; or (b) the MuCP is inserted in the 5' to 3' position into the bcx.

A preferred method further comprises modifying a Mu transposon using polymerase chain reaction (PCR) techniques to create the MuCP transposon, wherein conventional PCR techniques were used to append NdeI and EcoRI restriction sites at the 5' and 3' ends of a pDIMN2 vector containing the gene sequence coding for alpha synuclein, to create linearized pDIMN2. The MuCP transposon forms a complex with MuA transposase called the transposome, which then inserts itself into the target bcx. The design of MuCP-ISSC and MuCP-ISC does not need to be altered based on the target protein.

In preferred embodiments, the MuCP in not included in the circular permuted protein.

The foregoing description of the preferred embodiments and the appended figures have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

REFERENCES

1. Qian, Z., Fields, C. J., and Lutz, S. (2007) *Chem Bio Chem* 8, 1989-1996.
2. Goldenberg, D. P., and Creighton, T. E. (1983) *J Mol Biol* 165, 407-413.
3. Whitehead, T. A., Bergeron, L. M., and Clark, D. S. (2009) *Protein Eng Des Sel* 22, 607-613.
4. Markert, Y., Koditz, J., Mansfeld, J., Arnold, U., and Ulbrich-Hofmann, R. (2001) *Protein Eng* 14, 791-796.
5. Qian, Z., and Lutz, S. (2005) *J Am Chem Soc* 127, 13466-13467.
6. Guntas, G., Mansell, T. J., Kim, J. R., and Ostermeier, M. (2005) *Proc Natl Acad Sci USA* 102, 11224-11229.
7. Guntas, G., Kanwar, M., and Ostermeier, M. (2012) *PLoS One* 7, e35998.
8. McCullum, E. O., Williams, B. A., Zhang, J., and Chaput, J. C. (2010) *Methods in molecular biology* 634, 103-109.
9. Ihssen, J., Kowarik, M., Wiesli, L., Reiss, R., Wacker, M., and Thony-Meyer, L. (2012) *BMC biotechnology* 12, 67.
10. Crameri, A., Raillard, S. A., Bermudez, E., and Stemmer, W. P. (1998) *Nature* 391, 288-291.
11. Edelheit, O., Hanukoglu, A., and Hanukoglu, I. (2009) *BMC biotechnology* 9, 61.
12. Yu, Y., and Lutz, S. (2011) *Trends in biotechnology* 29, 18-25.
13. Krishna, M. M., and Englander, S. W. (2005) *Proc Natl Acad Sci USA* 102, 1053-1058.
14. Beernink, P. T., Yang, Y. R., Graf, R., King, D. S., Shah, S. S., and Schachman, H. K. (2001) *Protein science: a publication of the Protein Society* 10, 528-537.
15. Pieper, U., Hayakawa, K., Li, Z., and Herzberg, O. (1997) *Biochemistry* 36, 8767-8774.
16. Reitinger, S., Yu, Y., Wicki, J., Ludwiczek, M., D'Angelo, I., Baturin, S., Okon, M., Strynadka, N. C., Lutz, S., Withers, S. G., and McIntosh, L. P. (2010) *Biochemistry* 49, 2464-2474.
17. Feliu, J. X., and Villaverde, A. (1998) *FEBS Lett* 434, 23-27.
18. Guntas, G., and Ostermeier, M. (2004) *Journal of molecular biology* 336, 263-273.
19. Biondi, R. M., Baehler, P. J., Reymond, C. D., and Veron, M. (1998) *Nucleic Acids Res* 26, 4946-4952.
20. Tullman, J., Guntas, G., Dumont, M., and Ostermeier, M. (2011) *Biotechnol Bioeng* 108, 2535-2543.
21. Mehta, M. M., Liu, S., and Silberg, J. J. (2012) *Nucleic Acids Res* 40, e71.

22. Jones, D. D. (2005) *Nucleic acids research* 33, e80.
23. Sheridan, D. L., Berlot, C. H., Robert, A., Inglis, F. M., Jakobsdottir, K. B., Howe, J. R., and Hughes, T. E. (2002) *BMC neuroscience* 3, 7.
24. Haapa, S., Taira, S., Heikkinen, E., and Savilahti, H. (1999) *Nucleic acids research* 27, 2777-2784.
25. Goryshin, I. Y., Jendrisak, J., Hoffman, L. M., Meis, R., and Reznikoff, W. S. (2000) *Nature biotechnology* 18, 97-100.
26. Shah, V., Pierre, B., and Kim, J. R. (2013) *Anal Biochem* 432, 97-102.
27. Pierre, B., Xiong, T., Hayles, L., Guntaka, V. R., and Kim, J. R. (2011) *Biotechnol Bioeng* 108, 1011-1020.
28. Prentki, P., and Krisch, H. M. (1984) *Gene* 29, 303-313.
29. Gregory, J. A., Becker, E. C., Jung, J., Tuwatananurak, I., and Pogliano, K. (2010) *PLoS One* 5, e8731.
30. Baker, T. A., and Mizuuchi, K. (1992) *Genes Dev* 6, 2221-2232.
31. Goldhaber-Gordon, I., Early, M. H., and Baker, T. A. (2003) *Biochemistry* 42, 14633-14642.
32. Clancy, S., and Brown, W. (2008) *Nature Education* 1.
33. Kanwar, M., Wright, R. C., Date, A., Tullman, J., and Ostermeier, M. (2013) *Methods in enzymology* 523, 369-388.
34. Graf, R., and Schachman, H. K. (1996) *Proc Natl Acad Sci USA* 93, 11591-11596.

What is claimed is:

1. A method for designing circular permuted proteins, comprising constructing random circular permuted proteins using two engineered Mu transposons.

2. The method of claim 1, wherein at least one of the Mu transposons has an NdeI site at the 5' end of the Mu transposon and (a) an AgeI restriction site at the 3' end of the Mu transposon or (b) an AflIII site at the 3' end of the Mu transposon.

3. The method of claim 2, wherein the NdeI site is located inside of the TG recognition nucleotides.

4. The method of claim 3, wherein the NdeI site serves as a start codon for the protein that will be circularly permuted.

5. The method of claim 4, wherein the AflIII site serves as a stop codon that terminates translation of the circular permuted protein.

6. The method of claim 1, wherein each of the transposons contains unique restriction sites that serve to create sticky ended circular permuted DNA that ligates to a host vector.

7. The method of claim 6, wherein each of the transposons contains unique restriction sites that serve to create sticky ended circular permuted DNA of *Bacillus Circulans* (bcx) that ligates to a host vector pDIMN2.

8. The method of claim 6, wherein the two engineered Mu transposons are Mu Circular permutation transposon with Integrated Start Codon (MuCP-ISC) and Mu Circular permutation transposon with Integrated Start and Stop Codon (MuCP-ISSC).

9. The method of claim 8, further comprising restricting the length of the appended amino acids to 1 at N-terminus for both MuCP-ISSC and MuCP-ISC and to 2 and 3 at C-terminus for MuCP-ISSC and MuCP-ISC, respectively.

10. The method of claim 9, further comprising giving flexibility to the length of the linker sequence connecting the N and C termini.

11. The method of claim 10, wherein the transposon forms a complex with MuA transposase called the transposome, which then inserts itself into the target bcx.

12. The method of claim 7, wherein the restriction sites serve for sticky end ligation.

13. The method of claim 11, wherein integrated transposon restriction sites, further downstream of the process, serve as or comprise part of a start and stop codon that terminates translation.

14. The method of claim 13, wherein the MuCP is not included in the circular permuted protein.

15. The method of claim 8, wherein the design of MuCP-ISSC and MuCP-ISC does not need to be altered based on the target protein.

16. A method for designing circular permuted proteins, comprising:
    a) constructing random circular permuted proteins using a Mu Circular permutation transposon (MuCP);
    b) restricting the length of the appended amino acids to 1 at N-terminus for the MuCP and to 2 or 3 at C-terminus for the MuCP;
    c) comprising giving flexibility to the length of the linker sequence connecting the N and C termini for the MuCP.

17. The method of claim 16, wherein the MuCP is selected from the group consisting of Mu Circular permutation transposon with Integrated Start Codon (MuCP-ISC) and Mu Circular permutation transposon with Integrated Start and Stop Codon (MuCP-ISSC).

18. The method of claim 17, wherein each of the MuCPs contains unique restriction sites that serve to create sticky ended circular permuted DNA of *Bacillus Circulans* (bcx) that ligates to a host vector pDIMN2.

19. The method of claim 18, further comprising restricting the length of the appended amino acids to 1 at N-terminus for both MuCP-ISSC and MuCP-ISC and to 2 and 3 at C-terminus for MuCP-ISSC and MuCP-ISC, respectively.

20. The method of claim 19, further comprising giving flexibility to the length of the linker sequence connecting the N and C termini.

21. The method of claim 17, wherein:
    a) the MuCP-ISC is constructed by replacing a bcII site at the 5' end of the Mu transposon with an NdeI site, located inside of the TG recognition nucleotides, wherein the NdeI restriction site for the MuCP transposon serves as a start codon for the protein that will be circularly permuted, and wherein the AgeI restriction site at the 3' end of the Mu transposon remains unchanged; and
    b) the MuCP-ISSC is constructed by replacing a bcII site at the 5' end of the Mu transposon with an NdeI site, located inside of the TG recognition nucleotides, wherein the NdeI restriction site for the MuCP transposon serves as a start codon for the protein that will be circularly permuted, and replacing the AgeI restriction site at the 3' end of the Mu transposon with an AflIII site, which serves as a stop codon that terminates translation of the circular permuted protein.

22. The method of claim 18, wherein:
    a) the MuCP is mixed with MuA transposase and pDMIN2-bcx and subjected to digestion with SpeI to create sticky ended bcx-MuCP-ISC;
    b) the sticky ended bcx-MuCP is subjected to self ligation to create cyclized bcx-MuCP; and
    c) the cyclized bcx-MuCP is digested with NdeI and AgeI to form sticky ends and the MuCP removed.

23. The method of claim 18, wherein:
    a) the MuCP is inserted in the 3' to 5' position into the bcx; or
    b) the MuCP is inserted in the 5' to 3' position into the bcx.

24. The method of claim 16, further comprising modifying a Mu transposon using polymerase chain reaction (PCR) techniques to create the MuCP transposon, wherein conventional PCR techniques were used to append NdeI and EcoRI restriction sites at the 5' and 3' ends of a pDIMN2 vector containing the gene sequence coding for alpha synuclein, to create linearized pDIMN2.

25. The method of claim 24, wherein the MuCP transposon forms a complex with MuA transposase called the transposome, which then inserts itself into the target bcx.

26. The method of claim 25, wherein the design of MuCP-ISSC and MuCP-ISC does not need to be altered based on the target protein.

27. The method of claim 22, wherein the MuCP in not included in the circular permuted protein.

* * * * *

SEQUENCE LISTING

```
<160> NUMBER OF SEQ ID NOS: 35

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atgcagtatc                                                                10

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tggactagtg cc                                                             12

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtatctgaac cggtaa                                                         16

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcaaacgg                                                                10

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
aacggtgaac cggtaa                                                       16

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgcatccgg                                                              10

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tccggtgaac cggtaa                                                       16

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atgcacccgt                                                              10

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cccgttgaac cggtaa                                                       16

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atgcacctga                                                              10

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 11
cctgatgaac cggtaa                                                                                          16

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgcacgcca                                                                                                 10

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgccatgaac cggtaa                                                                                          16

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atgcacgact                                                                                                 10

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgacttgaac cggtaa                                                                                          16

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgcaagata                                                                                                 10

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agatatgaac cggtaa 16

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atgcaaccac 10

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
accactgaac cggtaa 16

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atgcaaatgc 10

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatgctgaac cggtaa 16

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgaaccggta a 11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttaccggttc a                                                            11

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgtgcaccgg ttca                                                         14

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgcatatgcg c                                                            11

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgaaccggtc gacg                                                         14

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgcatatgc a                                                            11

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgcctatgc a                                                            11

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaaccggtg cacg                                                         14

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgaagcggcg c                                                             11

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgtgcgccgc ttca                                                          14

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgccgcttc a                                                             11

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgaagcggcg cacg                                                          14

<210> SEQ ID NO 34
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatcttgcat atgggcgcac gaaaaacgcg aaagcgtttc acgataaatg cgaaaacgat        60
gtctaactcc agccaccgtt taaacggatc cttttcgacc gaataaatac ctgtgacgga       120
agatcacttc gcagaataaa taatcctggt gtccctgtt gataccggga agccctgggc        180
caacttttgg cgaaaatgag acgttgatcg gcacgtaaga ggttccaact ttcaccataa       240
tgaaataaga tcactaccgg gcgtattttt tgagttgtcg agattttcag gagctaagga      300
agctaaaatg gagaaaaaaa tcactggata taccaccgtt gatatatccc aatggcatcg      360
taaagaacat tttgaggcat ttcagtcagt tgctcaatgt acctataacc agaccgttca      420
gctggatatt acggcctttt taagaccgt aaagaaaaat aagcacaagt tttatccggc       480
ctttattcac attcttgccc gcctgatgaa tgctcatccg gaattacgta tggcaatgaa      540

-continued

```
agacggtgag ctggtgatat gggatagtgt tcacccttgt tacaccgttt tccatgagca      600
aactgaaacg ttttcatcgc tctggagtga ataccacgac gatttccggc agtttctaca      660
catatattcg caagatgtgg cgtgttacgg tgaaaacctg gcctatttcc ctaaagggtt      720
tattgagaat atgttttcg tctcagccaa tccctgggtg agtttcacca gttttgattt       780
aaacgtggcc aatatggaca acttcttcgc ccccgttttc accatgggca aatattatac      840
gcaaggcgac aaggtgctga tgccgctggc gattcaggtt catcatgccg tttgtgatgg      900
cttccatgtc ggcagaatgc ttaatgaatt acaacagtac tgcgatgagt ggcagggcgg      960
ggcgtaattt ttttaaggca gttattggtg cccttaaacg cctggttgct acgcctgaat     1020
aagtgataat aagcggatga atggcagaaa ttcgaaagca aattcgaccc ggtcgtcggt     1080
tcagggcagg gtcgttaaat agccgcttat gtctattgct ggtttaccgg tttattgact     1140
accggaagca gtgtgaccgt gtgcttctca aatgcctgag gccagtttgc tcaggctctc     1200
cccgtggagg taataattga cgataggatc cgcggccgcc gacacactcc aatctttccg     1260
ttttcgcatt tatcgtgaaa cgctttcgcg ttttttcgtgc accggttcaa ctag           1314
```

<210> SEQ ID NO 35
<211> LENGTH: 1205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
gatcttgcat atgcgcacga aaacgcgaaa agcgtttcac gataaatgcg aaaacgatgt       60
ctaactccag ccaccgttta aacggatcct agtaagccac gttgtgtctc aaaatctctg      120
atgttacatt gcacaagata aaaatatatc atcatgaaca ataaaactgt ctgcttacat      180
aaacagtaat acaaggggtg ttatgagcca tattcaacgg gaaacgtctt gctcgaggcc      240
gcgattaaat tccaacatgg atgctgattt atatgggtat aaatgggctc gcgataatgt      300
cgggcaatca ggtgcgacaa tctatcgatt gtatgggaag cccgatgcgc cagagttgtt      360
tctgaaacat ggcaaaggta gcgttgccaa tgatgttaca gatgagatgg tcagactaaa      420
ctggctgacg gaatttatgc ctcttccgac catcaagcat tttatccgta ctcctgatga      480
tgcatggtta ctcaccactg cgatccccgg gaaaacagca ttccaggtat tagaagaata      540
tcctgattca ggtgaaaata ttgttgatgc gctggcagtg ttcctgcgcc ggttgcattc      600
gattcctgtt tgtaattgtc cttttaacag cgatcgcgta tttcgtctcg ctcaggcgca      660
atcacgaatg aataacggtt tggttgatgc gagtgatttt gatgacgagc gtaatggctg      720
gcctgttgaa caagtctgga agaaaatgca taagcttttg ccattctcac cggattcagt     780
cgtcactcat ggtgatttct cacttgataa ccttattttt gacgagggga aattaatagg     840
ttgtattgat gttggacgag tcggaatcgc agaccgatac caggatcttg ccatcctatg     900
gaactgcctc ggtgagtttt ctccttcatt acagaaacgg cttttcaaa aatatggtat      960 tgataatcct gatatgaata aattgcagtt tcatttgatg ctcgatgagt ttttctaatc    1020
agaattggtt aattggttgt aacactggca gagcattacg ctgacttgac gggacggcgg    1080
ctttgttgaa taaatcgaac tttattcggt cgaaaaggat ccgcggccgc cgacacactc    1140
caatctttcc gttttcgcat ttatcgtgaa acgctttcgc gttttttcgtg ccttaagtca    1200 actag                                                                 1205
```